United States Patent [19]
Kenmochi et al.

[11] Patent Number: 5,959,161
[45] Date of Patent: Sep. 28, 1999

[54] METHOD FOR PRODUCING PARA-MENTHANE-3,8-DIOL

[75] Inventors: Hiroyuki Kenmochi; Teruyoshi Akiyama; Yoshifumi Yuasa; Toyohiko Kobayashi; Akio Tachikawa, all of Kanagawa, Japan

[73] Assignee: Takasago International Corporation, Tokyo, Japan

[21] Appl. No.: 09/179,688

[22] Filed: Oct. 27, 1998

[30] Foreign Application Priority Data

Oct. 28, 1997 [JP] Japan .................................. 9-311063

[51] Int. Cl.$^6$ .................................................. C07C 45/45
[52] U.S. Cl. ............................................................ 568/833
[58] Field of Search ............................................... 568/833

[56] References Cited

U.S. PATENT DOCUMENTS 5,298,250  3/1994  Lett et al. ............................... 424/405

OTHER PUBLICATIONS

Zimmerman et al, JACS, vol. 75, pp. 2367–2370, 1953.

*Primary Examiner*—James H. Reamer
*Attorney, Agent, or Firm*—Sughrue, Mion, Zinn, Macpeak & Seas, PLLC

[57] ABSTRACT

To offer a method of producing useful para-menthane-3,8-diol having the excellent repellent action to harmful living things, including noxious insects, in high purity and high yield, simply, and economically by the use of citronellal as a raw material compound.

The above-mentioned problems are resolved by the production method of this invention wherein citronellal is treated with aqueous sulfuric acid solution of 0.02 to 1.0 wt. % in concentration to produce para-menthane-3,8-diol. In case of recovering the produced para-menthane-3,8-diol, a method is preferably adopted, wherein after the reaction product is extracted with an aliphatic hydrocarbon solvent of 5 to 8 in carbon number, the extract is cooled down at temperature higher than the melting point of said aliphatic hydrocarbon solvent and of −10° C. or less to crystallize para-menthane-3,8-diol.

5 Claims, No Drawings

METHOD FOR PRODUCING PARA-MENTHANE-3,8-DIOL

BACKGROUND OF THE INVENTION

1. Field of the Invention

The present invention relates to a method for producing para-menthane-3,8-diol, and more particularly to a method for producing high-purity para-menthane-3,8-diol in high yield, effectively, and economically using citronellal as a raw material.

2. Prior Art

There are many diseases carried or caused by bloodsucking noxious insects, including ticks and mosquitoes, or other harmful living things. For example, mosquitoes cause malaria and yellow fever, fleas pest and eruption fever, and tsutsugamushi mites tsutsugamushi disease and others. Furthermore, even in case of not suffering such diseases, injuries of eruption, dermatitis and so on caused by mosquitoes, fleas, ticks and others are exceedingly heavy. Insecticides have been widely used for the prevention of the breeding and extermination of harmful living things including noxious insects from old times. However, there are some problems such as the appearance of tolerance to drugs due to misuse of insecticides, damages on human beings and animals from insecticides, and others. Moreover, under the present conditions, the prevention of the breeding and extermination of harmful living things can not be always done completely by insecticides.

Accordingly, instead of the prevention of the breeding and extermination of harmful living things, including noxious insects, through killing and wounding them, repellents which repel harmful living things to result in the prevention of the breeding and extermination of them have attracted public attention in recent years. Although various kinds of compounds, including para-menthane-3,8-diol, dialkyl phthalate and 2-ethyl-1,3-hexanediol, are known as compounds having the repellent action to noxious insects, among the compounds, para-menthane-3,8-diol is considered to be one of useful repellent compounds because of its high repellent action to noxious insects.

Para-menthane-3,8-diol is contained in leaves of eucalyptuses and can be obtained by extracting from leaves of eucalyptuses. However, extraction thereof from leaves of eucalyptuses is greatly restricted in points of raw material and the like, and it is difficult to obtain it in large quantities and economically. Consequently, methods for producing para-menthane-3,8-diol by chemical synthesis have been proposed. And in hitherto known methods of producing para-menthane-3,8-diol,is as follows;

Citronellal is treated with aqueous sulfuric acid solution of 5 weight % (hereinafter referring to wt. %) in concentration at room temperature to cause the ring closure of citronellal. Then, after the reaction product is extracted with ether or toluene, para-menthane-3,8-diol is obtained by distilling the extract under reduced pressures (J. Am. Chem. Soc., 75, 2367 (1953), examined Japanese Patent Publication 3-80138 and U.S. Pat. No. 5,298,250).

However, in case where the above-mentioned usual method is used, the purity of obtained para-menthane-3,8-diol is low, and the yield of the para-menthane-3,8-diol is not sufficiently high. Because acetal substances which are dehydrated condensation products from para-menthane-3,8-diol and citronellal are produced as by-products in large quantities together with para-menthane-3,8-diol. Consequently, high-purity para-menthane-3,8-diol can not be obtained in high yield, effectively and economically.

SUMMARY OF THE INVENTION

Accordingly, the object of this invention is to provide a method for producing para-menthane-3,8-diol having the excellent repellent action to harmful living things, including noxious insects, in high purity and yield, effectively and economically.

The inventors find that the production of the acetal substances, which are dehydrated condensation products from para-menthane-3,8-diol and citronellal is greatly reduced, resulting in obtaining high-purity para-menthane-3,8-diol in high yield, if considerably more dilute aqueous sulfuric acid solution than usual one, that is, aqueous sulfuric acid solution of 0.02 to 1 wt. % in concentration, instead of using that of 5 or more wt. % in concentration is used.

Furthermore, the inventors find that, high-purity para-menthane-3,8-diol will be obtained extremely smoothly in high productivity and economically without using such complicated apparatus and purification processes as those used in the above-mentioned usual production method, if the reaction product obtained by treating citronellal with sulfuric acid solution of 0.02 to 1 wt. % in concentration is extracted with an aliphatic hydrocarbon solvent of 5 to 8 in carbon number and then the obtained extract is cooled down at temperatures ranging from the temperature higher than the melting point of the aliphatic hydrocarbon solvent to the temperature of $-10°$ C. or less to crystallize para-menthane-3,8-diol.

That is, this invention is a method for producing para-menthane-3,8-diol which is characterized by producing para-menthane-3,8-diol comprising the step of treating citronellal with aqueous sulfuric acid solution of 0.02 to 1.0 wt. % in concentration.

And this invention comprises the method for producing para-menthane-3,8-diol as a preferred aspect, the method comprises the steps of (i) treating citronellal with aqueous sulfuric acid solution of 0.02 to 1.0 wt. % in concentration, (ii) extracting the reaction product from the process (i) with an aliphatic hydrocarbon solvent of 5 to 8 in carbon number, and (iii) cooling the extract from the process (ii) at temperatures ranging from the temperature higher than the melting point of said aliphatic hydrocarbon solvent to the temperature of $-10°$ C. or less to crystallize para-menthane-3,8-diol.

DETAILED DESCRIPTION OF THE INVENTION

This invention will be described in detail in the following.

Citronellal used as a raw material in this invention is also called a rhodinal and is colorless liquid of 204 to 206° C. in boiling point with aroma like that of a lemon. Citronellal can be obtained by purifying essential oils containing citronellal, that is, citronella oil, melissa oil and the like. There exist (+)-citronellal, (−)-citronellal and racemic citronellal. In the method of this invention, (+)-citronellal or racemic citronellal is preferably used, but (+) -citronellal is more preferably used.

As shown in the following chemical formulas, (+)-citronellal is indicated by the chemical formula (1). When (+)-citronellal is treated with aqueous sulfuric acid solution, the ring closure of citronellal is caused by the catalytic action of sulfuric acid, and normal-cis-para-menthane-3,8-diol of formula (2a) and normal-trans-para-menthane-3,8-diol of formula (2b) are mainly produced, and as small amount components, iso-cis-para-menthane-3,8-diol of formula (2c) and iso-trans-para-menthane-3,8-diol of formula (2d) are produced. In addition, as main by-products, acetal substances indicated by the chemical formula (3a) or (3b), condensation products from para-menthane-3,8-diol and citronellal, are produced.

sulfuric acid solution at once. Among the methods, the method of gradually adding citronellal in aqueous sulfuric acid solution is preferably adopted from the point of view of the possibility of obtaining the high yield of high-purity

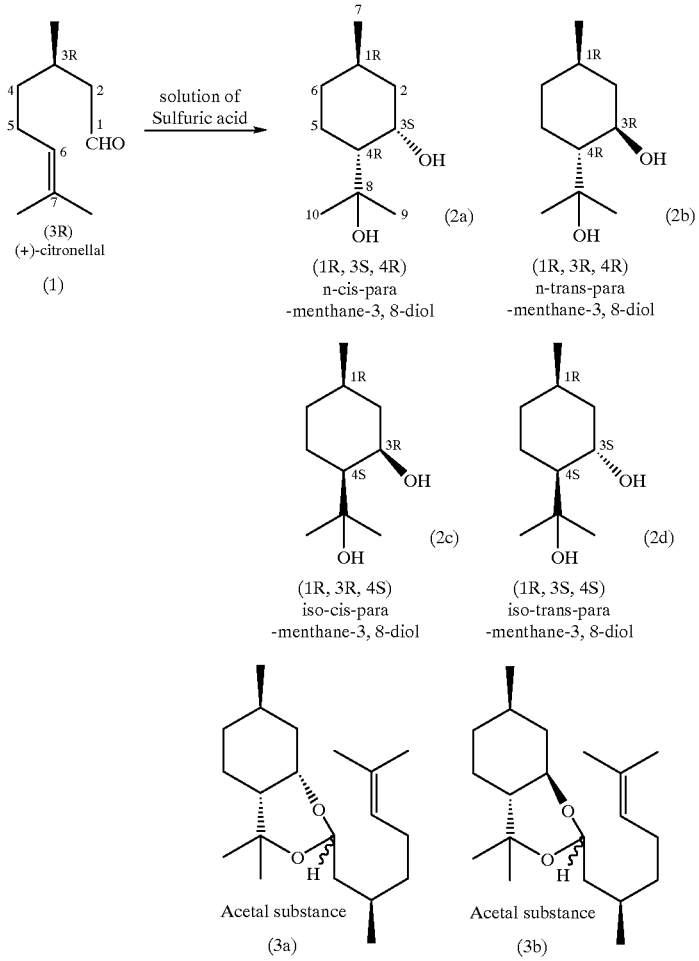

Formula 1 para-menthane-3,8-diol and the small amount of by-products and others.

In the method of this invention, it is required to treat citronellal with aqueous sulfuric acid solution of 0.02 to 1 wt. % in concentration. If the concentration of the aqueous sulfuric acid solution is less than 0.02 wt. %, the reactivity of citronellal will be low, and consequently, para-menthane-3,8-diol will be difficult to be selectively produced and its yield will be reduced. On the other hand, if the concentration of aqueous sulfuric acid solution is over 1 wt. %, the production amount of the by-product acetal substances of formula (3a) or (3b) will be increased and the purity of para-menthane-3,8-diol will be lowered. It is preferable to use aqueous sulfuric acid solution of 0.02 to 0.5 wt. % in concentration because para-menthane-3,8-diol with higher purity can be obtained in higher selectivity and in high yield.

As a method of treating citronellal with aqueous sulfuric acid solution, it is possible to adopt any of various methods, including a method of gradually adding citronellal in aqueous sulfuric acid solution, a method of gradually adding aqueous sulfuric acid solution in citronellal and a method of mixing both of the whole amounts of citronellal and aqueous As the ratio of aqueous sulfuric acid solution to citronellal, it is preferable to use 1 to 5 weight parts of aqueous sulfuric acid solution to 1 weight part of citronellal from the point of view of obtaining para-menthane-3,8-diol in high selectivity, and more preferable to use 1 to 4 weight parts of aqueous sulfuric acid solution.

Moreover, as temperatures when citronellal is treated with aqueous sulfuric acid solution, temperatures in the range of from ordinary temperature to 100 ° C. can be adopted. Temperatures of 50 to 60° C. are preferably adopted to produce para-menthane-3,8-diol in higher yield and thermal efficiency.

Although reaction time is not restricted especially, it is generally preferable to be in the range of 3 to 24 hours from the point of view of the yield of the para-menthane-3,8-diol, the reaction efficiency and the like, and more preferable to be in the range of 4 to 20 hours.

As a method of obtaining para-menthane-3,8-diol from the reaction product (the reaction liquid) prepared by treating citronellal with aqueous sulfuric acid solution, it is possible to adopt a method of distilling the reaction liquid directly under reduced pressures, to adopt a method of extracting the reaction product with an organic solvent at first and of distilling the extract then under reduced pressures or to adopt other previously known methods. However, it is preferable to adopt a method of extracting the reaction products with an organic solvent at first, and of crystallizing para-menthane-3,8-diol from the extract. In case of the methods comprising distillation to purify the para-menthane-3,8-diol, a packed distillation column is put side by side preferably.

In conducting the above-mentioned method of crystallizing para-menthane-3,8-diol from the extract obtained by treating the reaction product with an organic solvent, it is preferable to conduct said extraction treatment and crystallization using an aliphatic hydrocarbon solvent of 5 to 8 in carbon number as an organic solvent because high-purity para-menthane-3,8-diol can be obtained in high yield, easily and in high productivity. And in that case, para-menthane-3,8-diol is produced according to the above-mentioned preferable method of this invention; said preferable method comprises (i) a process of treating citronellal with aqueous sulfuric acid solution of 0.02 to 1 wt. % in concentration, (ii) a process of extracting the reaction product from said process (i) with an aliphatic hydrocarbon solvent of 5 to 8 in carbon number, and (iii) a process of cooling the extract recovered from said process (ii) down at temperatures higher than the melting point of said aliphatic hydrocarbon solvent and of −10° C. or less.

As for an aliphatic hydrocarbon solvent of 5 to 8 in carbon number to be used in said extraction process (ii), any of saturated or unsaturated aliphatic hydrocarbon solvents of 5 to 8 in carbon number can be used. However, saturated aliphatic hydrocarbon solvents of 5 to 8 in carbon number are preferably used. Moreover, although any of straight-chain or branched saturated aliphatic hydrocarbon solvents of 5 to 8 in carbon number can be used, straight-chain saturated aliphatic hydrocarbon solvents are preferably used. To be concrete, n-pentane, n-hexane, n-heptane, and n-octane can be given. It is allowed to use only one kind of aliphatic hydrocarbon solvents of 5 to 8 in carbon number or to use 2 or more kinds of the solvents at the same time. Among the solvents, n-heptane is preferably used.

In case of using aromatic hydrocarbon solvents like benzene, toluene, xylene and others as a solvent for extraction and crystallization, it is difficult to crystallize para-menthane-3,8-diol, in high purity and yield, because aromatic hydrocarbon solvents have a high affinity for para-menthane-3,8-diol.

In conducting the extraction treatment of the reaction product by using an aliphatic hydrocarbon solvent of 5 to 8 in carbon number, it is preferable to conduct the extraction treatment of the reaction liquid with an aliphatic hydrocarbon solvent of 5 to 8 in carbon number after keeping the reaction liquid pH over 7, preferably to be an alkaline solution pH in the range of 8 to 12 by adding alkali (for example, sodium hydroxide aqueous solution and so on) in the reaction liquid (the reaction product) containing para-menthane-3,8-diol. Thus, para-menthane-3,8-diol can be smoothly extracted in the aliphatic hydrocarbon solvent of 5 to 8 in carbon number. The amount of an aliphatic hydrocarbon solvent of 5 to 8 in carbon number to be used in the extraction treatment is preferable to be 100 to 300 weight parts to 100 weight part of said alkalized reaction liquid. Furthermore, temperatures in the range from ordinary temperature to 80° C. are preferably adopted as a temperature for the extraction.

Next, after separating and recovering from the water phase, the aliphatic hydrocarbon solvent phase is washed with water as occasion demands, moreover, for example, water contained in the aliphatic hydrocarbon solvent is removed by means of vacuum concentration and the like, the aliphatic hydrocarbon solvent phase is cooled down at temperatures higher than the melting point of the aliphatic hydrocarbon solvent and of −10° C. or less and para-menthane-3,8-diol is crystallized and separated from the aliphatic hydrocarbon solvent [the above-mentioned process (iii)].

Thus, para-menthane-3,8-diol can be obtained in high purity and yield. As for crystallization temperature, low-temperature crystallization temperatures in the range from −30° C. to −70° C. are preferably adopted, and more preferably temperatures in the range from −40° C. to −60° C. are adopted. In case where normal heptane is used as an aliphatic hydrocarbon solvent for extraction and crystallization, especially temperatures of −45° C. to −55° C. are preferably adopted. When crystallization temperature is over −30° C., crystallization may be insufficient depending on certain kinds of aliphatic hydrocarbon solvents. Moreover, when crystallization temperature is below −70° C., a large-scale crystallization apparatus is needed. According to experiments by the inventors of this invention, it has been confirmed that the ratio of cis-para-menthane-3,8-diol to trans-para-menthane-3,8-diol contained in the reaction product hardly changes before and after crystallization. The crystallization of para-menthane-3,8-diol from the aliphatic hydrocarbon solvent under a cooling condition is preferable to be conducted while stirring from the point of view of producing crystals which are easily filtered.

EXAMPLES

This invention will be concretely explained by examples and comparative examples in the following. This invention, however, should not be limited by those examples. Physical data in the following examples were measured by using following measuring instruments and measuring conditions. Furthermore, % in the following examples means weight % unless being specially noted.

(1) Measurement of the Conversion, the Selectivity of para-menthane-3,8-diol, cis/trans Ratio, and the Content Rate of Acetal Substances Measurement was made by gas chromatography.

Measuring instrument; [GC-9A] made by Shimazu Corporation.

Column; [Silicon NUTRABOND-1] made by GL Science Inc. (0.25 mm in inner diameter, 30 m in length).

Measuring conditions; Temperature was raised from 100° C. to 230° C. in the speed of 10° C./min.

(2) Optical Rotation

Instrument used; [Polarimeter DIP-4] made by Nihon Bunko Kougaku Inc.

(3) Nuclear Magnetic Resonance Spectrum $^1$H-NMR;

Instrument used; [AM-400Model] (400 MHz) made by Brucker Inc.

$^{13}$C-NMR;

Instrument used; [AM-400Model] (100 MHz) made by Brucker Inc.

Internal standard substance; Tetramethylsilane.

(4) Infrared Spectrum (IR)

Instrument used; [IR-810 Model] made by Nihon Bunko Kogyo Inc.

(5) Mass Spectrum (MS)

Instrument used; [M-80 Mass spectrometer] (Ionization voltage 20 eV) made by Hitachi Ltd.

Example 1

(1) In a 3 litter four-neck flask with a stirrer, a thermometer and a dropping funnel, 636 g (16.3 mMol) of aqueous sulfuric acid solution 0.25 wt. % in concentration [5 mMol equivalent weight to (+) -citronellal, the substrate] was charged and heated at 55° C. Then, after 500 g (3.24 Mol) of (+)-citronellal was dropped in the flask over 1 hour, the solution was kept and reacted at the same temperature for 9 hours.

(2) The minute amount of sample was taken from the reaction liquid obtained by the above-mentioned process (1) and measured by gas chromatography. As a result, the conversion of citronellal was 99.0%, the selectivity of para-menthane-3,8-diol in the reaction product was 92.3% (the total of cis form and trans form), and the production rate of acetal substances in the reaction product (the content rate)was 2.1%. In addition, cis/trans ratio in para-menthane-3,8-diol was measured by gas chromatography, resulting in 61.9/38.1.

(3) After 8 g of 25% sodium hydroxide aqueous solution (50 mMol) was added in the reaction liquid obtained by the above-mentioned process (1) to make the liquid alkali (pH 12), 1,000 g of normal-heptane was added and the extraction treatment of the reaction liquid was conducted under stirring. After being separated and recovered from water phase, the organic phase was washed with 500 g of water and separated. Then, the washed organic phase was heated and refluxed to remove water.

(4) The water removed organic phase obtained by the above-mentioned process (3) was cooled down to –50° C. and stirred at the same temperature for one night to precipitate crystals. Then, by filtering the crystals, 447 g of para-menthane-3,8-diol (the mixture of cis form and trans form) was obtained. When having been left as it was at room temperature, the crystals melted and became oily material.

(5) According to the gas chromatography measurement, the purity of para-menthane-3,B-diol obtained by the above-mentioned process (4) was 99.0% and the content rate of acetal substances was 0.15% (the yield of para-menthane-3,8-diol was 80%). This means that high-purity para-menthane-3,8-diol was obtained in high yield with the extremely lower content of acetal substances. Further, the cis/trans ration was measured to be 64.9/35.1 by gas chromatography. Moreover, the boiling point of para-menthane-3,8-diol obtained by the above-mentioned process (4) was 100 to 130° C./0.8 torr.(107 Pa), and its optical rotation $[\alpha]_D^{20}$ was +5.2° (neat).

(6) In addition, 25 g of para-menthane-3,8-diol obtained by the above-mentioned process (4) was purificated by a silica gel column chromatography (silica gel 500 g : a mixed solvent of ether and normal hexane) to give 5.2 g of cis form and 3.5 g of trans. Each of them was dissolved in the small quantity of ether, and then they were recrystallized using n-hexane. Physical properties of obtained cis-para-menthane-3,8-diol and trans-para-menthane-3,8-diol were measured. The results are as follows.

Physical properties of cis-para-menthane-3,8-diol

Melting point: 67° C.

$[\alpha]_D^{20}$=+15.4° (c=0.5, CHCl$_3$)$^1$H-NMR (CDCl$_3$, δ): 0.86–0.96(1H,m), 0.87(3H,d,J=6 Hz,CH$_3$), 1.05(1H,t,9 Hz), 1.13–1.18(1H,m), 1.22(3H,s,CH$_3$), 1.36(3H,s,CH$_3$), 1.64–1.86(5H,m), 2.97(1H,s), 3.25(1H,d,J=2 Hz), 4.40(1H, br,s).

$^{13}$C-NMR (CDCl$_3$,δ): 20.3(C-5), 22.2(C-7), 25.6(C-1), 28.7(C-10), 28.9(C-9), 34.9(C-6), 42.5(C-2), 48.3(C-4), 67.9(C-3), 73.2(C-8).

IRvmax (KBr): 3260 cm$^{-1}$

MS (m/e, %) 157 (M$^+$−15,4), 154 (M$^+$−18, 5), 139(11), 121(9), 111(7), 96(53), 81(100), 67(18), 59(62), 54(23), 43(34).

Physical properties of trans-para-menthane-3,8-diol

Melting point: 73° C.

$[\alpha]_D^{20}$=−14.4° (c=0.5, CHCl$_3$)

$^1$H-NMR (CDCl$_3$, δ): 0.84–0.98(2H,m), 0.92(3H,d,J=6.5 Hz,CH$_3$), 1.04(1H,q,J=11,24 Hz), 1.22(6H,s,2×CH$_3$), 1.35–1.49(2H,m), 1.63–1.73(2H,m), 1.92–1.97(1H,m), 3.71 (1H, m,CHOH), 3.95(1H,s,OH), 4.21(1H,d,J=3 Hz,OH).

$^{13}$C-NMR (CDCl$_3$, δ): 21.9(C-7), 23.5(C-10), 26.9(C-6), 29.7(C-9), 31.2(C-1), 34.5(C-5), 44.4(C-2), 53.0(C-4), 72.6 (C-3), 74.8(C-8).

IRvmax (KBr): 3260 cm$^{-1}$

MS (m/e, %): 157(M$^+$−15,1), 154(2), 139(9), 121(6), 114(4), 96(49), 81(100), 67(18), 59(79), 54(25), 43(16).

Example 2

(1) (+)-citronellal was dropped into aqueous sulfuric acid solution and reacted in the same method as (1) in Example 1, except for the change of the concentration of sulfuric acid, reaction temperature and reaction time.

(2) The small amount of sample was taken from the reaction product (the reaction liquid) obtained by the above-mentioned process (1) and measured by gas chromatography. As a result, the conversion of citronellal, the selectivity of para-menthane-3,8-diol in the reaction product (the total of cis form and trans form), the production rate of acetal substances and the yield of para-menthane-3,8-diol were as shown in the following table:

TABLE 1

| Experiment No. | Concentration of sulfuric acid[1] | Reaction temperature | Reaction time | Conversion | Selectivity | Production rate of acetal substances[2] |
| --- | --- | --- | --- | --- | --- | --- |
| 1 | 10% | 35° C. | 4 hour | 97.1% | 73.8% | 20.3% |
| 2 | 5% | 35° C. | 6 hour | 98.9% | 72.0% | 22.5% |
| 3 | 3% | 35° C. | 6 hour | 98.3% | 78.8% | 14.9% |
| 4 | 1% | 25° C. | 16 hour | 96.9% | 86.7% | 7.5% |
| 5 | 0.5% | 25° C. | 20 hour | 95.3% | 89.5% | 4.8% |
| 6 | 0.25% | 50° C. | 11 hour | 97.9% | 92.3% | 2.7% |
| 7 | 0.25% | 60° C. | 7 hour | 98.2% | 91.5% | 2.8% |
| 8 | 0.25% | 70° C. | 6 hour | 99.0% | 90.1% | 3.6% |

TABLE 1-continued

| Experiment No. | Concentration of sulfuric acid[1] | Reaction temperature | Reaction time | Conversion | Selectivity | Production rate of acetal substances[2] |
|---|---|---|---|---|---|---|
| 9  | 0.15% | 60° C.  | 10 hour | 97.8% | 91.7% | 1.9% |
| 10 | 0.05% | 60° C.  | 20 hour | 95.4% | 91.0% | 1.1% |
| 11 | 0.05% | 100° C. | 5 hour  | 98.7% | 87.7% | 2.0% |
| 12 | 0.02% | 100° C. | 10 hour | 97.4% | 87.4% | 1.5% |
| 13 | 0.01% | 100° C. | 20 hour | 97.5% | 80.8% | 2.7% |

[1]The concentration of aqueous sulfuric acid solution.
[2]The rate of dehydrated condensation products from para-menthane-3,8-diol and citronellal to the total weight of reaction products (the total quantity of produced compounds) obtained by making aqueous sulfuric acid solution act on (+)-citronellal.

From the results of the above-mentioned Table 1, in case of the experiments of No.4 to 12 in which para-menthane-3,8-diol was produced by making aqueous sulfuric acid solution of 0.02 to 1% in concentration act on citronellal, it is found that the production rate of by-product acetal substances is extremely low and high-purity para-menthane-3,8-diol is obtained, and that the selectivity of para-menthane-3,8-diol is extremely high as 86.7 to 92.3%. In particular, in the experiments of No. 5 to 12 in which aqueous sulfuric acid solution of 0.02 to 0.5% in concentration is used, the production rate of acetal substances is extremely low like 4.8% or less and higher-purity para-menthane-3,8-diol is obtained.

On the other hand, in the experiments of No. 1 to 3 in which aqueous sulfuric acid solution of 3% or more in concentration is used, it is found that the production rate of by-product acetal substances is about 15% or more, especially in the experiments of No. 1 and 2 in which the concentration of aqueous sulfuric acid solution is 5% or more, the production rate of acetal substances is more than 20% and extreme high in either case and the purity of obtained para-menthane-3,8-diol is low. Furthermore, it is found that in the experiments of No. 1 to 3, the selectivity of para-methane-3.8-diol is 78.8% or less, lower by about 8% or more compared with those in the experiments of No. 4 to 12, especially in the experiments of No. 1 and 2 in which the concentration of aqueous sulfuric acid solution is 5% or more, the selectivity of para-menthane-3,8-diol is 73.8% or less, lower by 13% or more compared with those in the experiments of No. 4 to 12.

In addition, in case of the experiment of No. 13 in which the concentration of aqueous sulfuric acid solution is 0.01%, even after the reaction of 20 hours at a high temperature of 100° C., the selectivity of para-menthane-3,8-diol is 80.8%, and it is found that in spite of a long time reaction at a high temperature, the selectivity of para-menthane-3,8-diol is about 6% lower compared with those in the experiments of No. 4 to 12.

Example 3

(1) (+)-citronellal was dropped into aqueous sulfuric acid solution and reacted in the same method as (1) in Example 1, except that 1,270 g (6.5mMol) of aqueous sulfuric acid solution 0.05% in concentration was used.

(2) The small amount of sample was taken from the reaction product (the reaction liquid) obtained by the above-mentioned process (1) and measured by gas chromatography. As a result, the conversion of citronellal was 96.0%, the selectivity of para-menthane-3,8-diol in the reaction product (the total of cis form and trans form) was 92.8%, the production rate of acetal substances was 0.6% and the yield of para-menthane-3,8-diol to (+)-citronellal was 79%. Consequently, high-purity para-menthane-3,8-diol with the extremely low content of acetal substances was obtained in high yield.

Example 4

(1) (+)-citronellal was dropped into aqueous sulfuric acid solution and reacted in the same method as (1) in Example 1, except that 1, 905g (4.86 mMol) of aqueous sulfuric acid solution 0.025% in concentration was used and the reaction was carried out for 20 hours.

(2) The small amount of sample was taken from the reaction product (the reaction liquid) obtained by the above-mentioned process (1) and measured by gas chromatography. As a result, the conversion of citronellal was 95.4%, the selectivity of para-menthane-3,8-diol in the reaction product (the total of cis form and trans form) was 92.3%, the production rate of acetal substances was 0.4% and the yield of para-menthane-3,8-diol to (+)-citronellal was 78%. Consequently, high-purity para-menthane-3,8-diol with the extremely low content of acetal substances was produced in high yield.

Comparative Example 1

(1) In a 3 litter flask with a stirrer, a thermometer and a dropping pipe, 636 g (324 mMol) of aqueous sulfuric acid solution 5% in concentration was charged and heated at 30° C. Then, after 500 g (3.24 Mol) of (+)-citronellal was dropped in the flask over 1 hour, the solution was kept and reacted at the same temperature for 6 hours.

(2) The small amount of sample was taken from the reaction product (the reaction liquid) obtained by the above-mentioned process (1) and measured by gas chromatography. As a result, the conversion of citronellal was 97.5%, the selectivity of para-menthane-3,8-diol in the reaction product (the total of cis form and trans form) was 73.9%, and the production rate of acetal substances was 18.6%.

(3) After 155 g (969 mMol) of 25% sodium hydroxide aqueous solution was added in the reaction product (the reaction liquid) obtained by the above-mentioned process (1) to make the liquid alkali (pH 12), 700 g of toluene was added and the extraction treatment of the reaction liquid was conducted under stirring. After being separated and recovered from water phase, the organic phase was washed with 600 g of water and separated. Then, the washed organic phase was concentrated under reduced pressure and 536 g of crude para-menthane-3,8-diol was obtained. Next, said crude para-menthane-3,8-diol was distilled and375.8 g of purified para-menthane-3,8-diol (a mixture of cis form and trans form) was obtained.

(4) According to the gas chromatography measurement, the purity of para-menthane-3,8-diol obtained by the above-mentioned process (3) was 96.1%, the content rate of acetal substances was 2.5%, and the yield of para-menthane-3,8-diol (the total of cis form and trans form) was low, that is, 67%. Further, the cis/trans ratio in para-menthane-3,8-diol was measured by gas chromatography, resulting in 64.7/35.3.

Moreover, the boiling point of para-menthane-3,8-diol obtained by the above-mentioned process (3) was 90 to 96° C./0.3 torr. (40 Pa), and its optical rotation $[\alpha]_D^{20}$ was +4.5° (neat).

In cases where the production method of this invention is used, useful para-menthane-3,8-diol having the excellent repellent action to harmful living things, including noxious insects, can be produced in high purity and yield, simply, and economically by the use of citronellal as a raw material compound.

In particular, in the production method of this invention, in cases where para-menthane-3,8-diol is separated and recovered by adopting a method in which the reaction product obtained by making aqueous sulfuric acid solution of 0.02 to 1 wt. % in concentration act on citronellal was extracted with an aliphatic hydrocarbon solvent of 5 to 8 in carbon number and thereby obtained extract was cooled down at temperatures higher than the melting point of said aliphatic hydrocarbon solvent and of −10° C. or less to crystallize para-menthane-3,8-diol, high-purity of para-menthane-3,8-diol can be obtained extremely smoothly, in high productivity and economically, without the need of such a complicated apparatus and purification process as in usual production methods which need distillation and purification processes.

What is claimed is:

1. A method for producing para-menthane-3,8-diol comprising the step of treating citronellal with an aqueous sulfuric acid solution of 0.02 to 1.0 weight % in concentration to produce para-menthane-3,8-diol.

2. A method according to claim 1, wherein said method further comprises the steps of (i) extracting the reaction product from said aqueous sulfuric acid treatment step with an aliphatic hydrocarbon solvent of 5 to 8 in carbon number, and (ii) cooling the extract recovered in said extraction step at temperatures ranging from the temperature higher than the melting point of said aliphatic hydrocarbon solvent to the temperature of −10° C. or less to crystallize para-menthane-3,8-diol.

3. A method according to claim 1 or 2, wherein citronellal is treated with an aqueous sulfuric acid solution of 0.02 to 0.5 weight % in concentration.

4. A method according to any one of claims 1 to 3, wherein citronellal is (+)-citronellal.

5. A method according to any one of claims 2 to 4, wherein an aliphatic hydrocarbon solvent is normal heptane and the extracted solution is cooled at temperatures ranging from −30° C. to −70° C. in the cooling step (ii).

* * * * *